US006471972B1

(12) United States Patent
Bonte et al.

(10) Patent No.: US 6,471,972 B1
(45) Date of Patent: Oct. 29, 2002

(54) COSMETIC TREATMENT METHOD FOR FIGHTING AGAINST SKIN AGEING EFFECTS

(75) Inventors: Frédéric Bonte, Orleans (FR); Marc Dumas, Orleans (FR); Catherine Heusele, Limours (FR); Jacques Le Blay, Leves (FR)

(73) Assignee: LVMH Recherche, Paris (FR)

(*) Notice: Subject to any disclaimer, the term of this patent is extended or adjusted under 35 U.S.C. 154(b) by 0 days.

(21) Appl. No.: 09/701,341

(22) PCT Filed: May 28, 1999

(86) PCT No.: PCT/FR99/01261

§ 371 (c)(1),
(2), (4) Date: Nov. 28, 2000

(87) PCT Pub. No.: WO99/62481

PCT Pub. Date: Dec. 9, 1999

Related U.S. Application Data

(63) Continuation-in-part of application No. 09/297,679, filed on May 6, 1999, now Pat. No. 6,193,975.

(30) Foreign Application Priority Data

Nov. 7, 1996 (FR) .............................................. 96 13585
May 29, 1998 (FR) .............................................. 98 06822

(51) Int. Cl.$^7$ ............................ A61K 7/48; A61K 7/40; A61K 35/00; A61K 33/32; A01N 65/00
(52) U.S. Cl. ....................... 424/401; 424/681; 424/682; 424/725; 424/773; 424/642; 424/59; 424/62; 424/74; 424/70.1; 424/70.9; 514/847; 530/379
(58) Field of Search ................................ 424/401, 642, 424/59, 62, 70.1, 70.9, 74, 725, 773, 681, 682; 514/847; 530/379

(56) References Cited

U.S. PATENT DOCUMENTS

| 4,938,969 A | 7/1990 | Schnintsky et al. ......... 424/642 |
| 5,804,168 A | 9/1998 | Murad ........................ 424/59 |

FOREIGN PATENT DOCUMENTS

| FR | 2 406 438 | | 5/1979 |
| FR | 2 669 225 | | 5/1992 |
| FR | 2 704 390 | | 11/1994 |
| FR | 2 713 483 | | 6/1995 |
| FR | WO 96/25143 | * | 8/1996 |
| FR | 2 735 981 | | 1/1997 |
| WO | 94/22421 | | 10/1994 |
| WO | 97/09963 | | 3/1997 |
| WO | 98/19664 | | 5/1998 |

OTHER PUBLICATIONS

Derwent Abstracted –Pub–No.: EP 558509B, Mar. 15, 1995, Bonte et al., Compositions for the hair and scalp prenventing hair loss.*

* cited by examiner

Primary Examiner—Frederick Krass
Assistant Examiner—Clinton Ostrup
(74) Attorney, Agent, or Firm—Gary M. Nath; Todd L. Juneau; Joshua B. Goldberg

(57) ABSTRACT

The present invention relates to a method of cosmetic treatment for combating the effects of skin ageing and to novel cosmetic compositions which are particularly suitable for carrying it out. According to the invention, at least one agent for promoting the adhesion of the keratinocytes of the epidermal baseal layer to the dermo-epidermal junction, especially to the collagen IV of said junction, such as, in particular, a divalent metal salt or complex, preferably magnesium aspartate or magnesium chloride, is used, optionally in association with a stimulant of collagen IV synthesis and/or a stimulant of collagen VII synthesis. The application is for the preparation of cosmetic compositions with anti-wrinkle activity.

17 Claims, No Drawings

COSMETIC TREATMENT METHOD FOR FIGHTING AGAINST SKIN AGEING EFFECTS

This application is a 371 of International Application No. PCT/FR99/01261, filed May 28, 1999, which claims priority to continuation-in-part U.S. application Ser. No. 09/297,679, now U.S. Pat. No. 6,193,975, filed May 6, 1999, French Application No. 98/06822, filed May 29, 1998, and French Application No. 96/13585, filed Nov. 7, 1996.

The present invention relates to a method of cosmetic treatment for combating the effects of skin ageing and to novel cosmetic compositions which are particularly suitable for carrying it out.

The dermo-epidermal junction (DEJ) is known to be a complex structure assuring the cohesion and exchanges between the dermis and epidermis which are essential for the skin to function properly.

It has been discovered that it is possible to slow down or treat skin ageing, and in particular to reduce the depth of wrinkles, and/or slow down their appearance, and/or restore the tonicity and elasticity of the skin, and/or slow down the decrease in tonicity and elasticity of the skin, by means of a method of cosmetic treatment corresponding to a novel concept which consists in using a cosmetically acceptable agent to promote the adhesion of the keratinocytes of the epidermal basal layer to the dermo-epidermal junction, especially to the type IV collagen, also called collagen IV, which is a major constituent of said dermo-epidermal junction. It is this discovery which constitutes the basis of the present invention.

Thus, according to its most general feature, the present patent application aims to cover a method of cosmetic treatment for slowing down or treating skin ageing, and in particular for reducing the depth of wrinkles, and/or slowing down their appearance, and/or restoring the tonicity and elasticity of the skin, and/or slowing down the decrease in tonicity and elasticity of the skin, characterized in that an amount of at least one agent for promoting the adhesion of the keratinocytes of the epidermal basal layer to the dermo-epidermal junction, especially to the collagen IV of said junction, is applied to the skin.

It has furthermore been shown that particularly remarkable results are obtained within the framework of the present invention if the above-mentioned adhesion promoter is applied in association with an effective amount of at least one stimulant of collagen IV synthesis and/or with an effective amount of at least one stimulant of collagen VII synthesis.

The expression "stimulant of collagen IV or collagen VII synthesis" is understood within the framework of the present description as meaning any agent which is capable of producing or maintaining a high level of collagen IV in the dermo-epidermal junction, either by increasing the biosynthesis or by inhibiting the enzymes which degrade the constituent proteins of this product.

In one advantageous embodiment of the invention, the above-mentioned adhesion promoter is a divalent metal salt or complex, particularly a magnesium or zinc salt or complex, or a mixture of divalent metal salts or complexes.

The divalent metal salt or complex is preferably a divalent metal chloride or a divalent metal salt or complex with a cosmetically acceptable organic acid such as an amino acid, for example aspartic acid, asparagine, proline, glutamic acid, methionine, leucine, histidine or lysine, or a $C_2$–$C_{12}$ aliphatic alpha-hydroxy acid, particularly citric acid, glycolic acid, gluconic acid, malic acid, lactic acid or 2-hydroxybutyric acid.

In one currently preferred embodiment of the invention, said divalent metal salt or complex is magnesium aspartate or magnesium chloride.

According to one particular characteristic of the method of the present invention, the above-mentioned adhesion promoter is applied in the form of a composition in which it is present in an amount of between 0.0001 and 5% by weight, preferably of between 0.001 and 1% by weight, based on the total weight of the composition.

Any stimulant of collagen IV synthesis can be used within the framework of the method according to the present invention.

In one currently preferred embodiment, the stimulant of collagen IV synthesis is selected from soya saponins and soya sapogenols, preferably of type A and type B, and plant extracts rich in such compounds, preferably extracts of soya (*Glycine max*) or alfalfa (*Medicago sativa*).

In another preferred embodiment, the stimulant of collagen IV synthesis is a whole range of saponins from roots of *Medicago sativa*.

Likewise, any stimulant of collagen VII synthesis can be used within the framework of the present invention.

In one currently preferred embodiment, the stimulant of collagen VII synthesis is an extract of *Potentilla erecta*.

In another preferred embodiment, the stimulant of collagen VII synthesis is an extract of Bertholletia, particularly *Bertholletia excelsa*.

According to a second feature, the present patent application aims to cover novel cosmetic compositions which are particularly suitable for carrying out the method described above.

These compositions are essentially characterized in that they contain an effective amount of at least one agent for promoting the adhesion of the keratinocytes of the epidermal basal layer to the dermo-epidermal junction, especially to the collagen IV of said junction, said agent being selected from magnesium or zinc salts or complexes, in association with an effective amount of at least one stimulant of collagen IV synthesis and/or an effective amount of at least one stimulant of collagen VII synthesis.

In these compositions, the various adhesion promoters and stimulants of collagen IV synthesis or collagen VII synthesis are as described above within the framework of the general description of the method according to the invention.

The compositions of the invention may also advantageously comprise at least one substance for promoting the synthesis of the constituents of the extracellular matrix of the skin.

Furthermore, the compositions according to the invention can also contain at least one substance selected from the group consisting of vitamins, particularly the vitamins of group A (retinol) and group C and derivatives thereof such as the esters, especially the palmitates and propionates, tocopherols, xanthines, particularly caffeine or theophylline, retinoids, particularly vitamin A acid, extracts of *Centella asiatica*, asiatic and madecassic acids and glycosylated derivatives thereof such as asiaticoside or madecassoside, extracts of *Siegesbeckia orientalis*, extracts of *Commiphora mukul* and extracts of *Eriobotrya japonica*, cosmetically acceptable silicon derivatives such as polysiloxanes, silanols and silicones, $C_3$–$C_{12}$ aliphatic alpha-keto acids, particularly pyruvic acid, $C_2$–$C_{12}$ aliphatic alpha-hydroxy acids, particularly citric acid, glycolic acid, malic acid and lactic acid, amino acids, particularly arginine, citrulline and threonine, ceramides, glycoceramides, sphingosine derivatives, particularly type II and III ceramides, phospholipids, forskolin and derivatives thereof, extracts of Coleus, extracts of Tephrosia, elastase inhibitors, particularly ellagic acid and soya peptides, collagenase inhibitors, particularly plant peptides and extracts such as extracts of roots of Coptidis and extracts of roots of *Scutellaria baicalensis Georgi*, flavonoids such as wogonin, baicalin and baicalein, aqueous-ethanolic extracts of leaves of *Ginkgo biloba, Mosla chinensis, Salvia officinalis* and *Cinnamomum cassia*, catechuic extracts of *Camellia sinensis* and aqueous extracts of bean shells of *Theobroma cacao*, anti-inflammatories, particularly phospholipase A2 inhibitors, soothing agents, particularly extracts of liquorice, glycyrrhetinic acid and ammonium glycyrrhizinate, hydrating agents, particularly polyols, propylene glycol, butylene glycol, glycerol and hyaluronic acid, agents for combating stretch marks, particularly extracts of horse chestnut and escin, agents for protecting or improving the microcirculation, particularly bioflavonoids from *Ginkgo biloba*, isodon, extracts of *Ami visnaga*, visnadine and ruscogenin, free radical inhibitors, particularly polyphenols such as PCO (procyanidolic oligomers) and derivatives thereof and plant extracts, particularly extracts of *Curcuma longa*, antiseborrhea agents, such as a 5-alpha-reductase inhibitor, particularly an extract of *Pygeum africanum*, and stimulants of the microcirculation of the blood, such as cepharanthine and methyl nicotinate.

The compositions according to the invention can advantageously contain substances for protecting the skin from the harmful effects of the sun, such as solar filters, individually or in combination, especially UV A filters and UV B filters, particularly titanium oxides and zinc oxides, oxybenzone, Parsol MCX, Parsol 1789 and filters of vegetable origin, substances for limiting the damage caused to the DNA, particularly those for limiting the formation of thymine dimers, such as ascorbic acid and derivatives thereof and/or Photonyl®, and substances for contributing to the elimination of liver spots, such as inhibitors of melanin or tyrosinase synthesis.

Other objects, characteristics and advantages of the invention will become clearly apparent to those skilled in the art from the following explanatory description referring to several Examples relating to tests performed, and Examples of cosmetic formulations, which are given simply by way of illustration and cannot therefore in any way limit the scope of the invention.

All the percentages are given by weight in the Examples, unless indicated otherwise.

EXAMPLE 1

Test for the Adhesion of Normal Human Keratinocytes to Type IV Collagen with the Aid of an Agent According to the Invention for Promoting the Adhesion of the Keratinocytes to the Dermo-epidermal Junction, Consisting of Magnesium Chloride or Aspartate in this Test The object of the present test is to demonstrate the efficacy of an agent according to the invention for promoting the adhesion of the keratinocytes to the dermo-epidermal junction, said agent preferably consisting of magnesium chloride or aspartate.

Within this framework, said test is carried out in the following manner:

1. Coating of the Adhesion Surfaces with type IV Collagen

Wells of microplates (Falcon) are covered with 6 $\mu g/cm^2$ of sterile type IV human collagen (from Sigma).

Each well is then incubated overnight at +4° C. with a 4 mg/ml solution of bovine albumin, BSA, from Sigma.

The wells are then rinsed twice with a phosphate buffer, PBS (phosphate buffered saline), from Gibco.

2. Preparation of the Cultures of Normal Human Keratinocytes

The epidermal cells are obtained from healthy surgical skin originating from the mammary region of a 53-year-old female caucasian donor.

The skin fragments are incubated in 0.25% w/v trypsin for 18 hours at +4° C. to separate the dermis and epidermis and to obtain, by agitation, a suspension of epidermal cells. The trypsin is neutralized with fetal calf serum, FCS, from Gibco.

The cells are inoculated into flasks defining a surface area of 75 $cm^2$ and are cultured in keratinocyte proliferation medium, K-SFM, from Gibco, to the point of confluence, when they are subcultured.

The cells used for the experiments for adhesion to the collagen substrate were not subcultured beyond the first subculture (called P0 or P1).

3. Treatment of the Keratinocytes with the Product of the Invention, Consisting of either Magnesium Chloride or Magnesium Aspartate Trypsin (trypsin containing 0.1% –0.02% w/v of EDTA, from Gibco) is added to the keratinocyte cultures, and the cell suspension is placed in E 199 medium from Gibco, complemented with 2 mM L-glutamine and 4 mg/ml of BSA and containing, according to the invention, 0.25, 0.5 or 1 mM magnesium chloride or 0.25 mM magnesium aspartate.

The keratinocytes are then incubated for 30 minutes at +4° C. before the step for adhesion to the substrate coated with collagen IV is carried out.

4. Measurement of the Adhesion of the Keratinocytes to the Type IV Collagen

The keratinocytes are inoculated into each well at a density of 93,000 cells/$cm^2$ in E 199 medium from Gibco, containing 2 mM L-glutamine from Gibco and 4 mg/ml of BSA (bovine serum albumin). After incubation for one hour at +4° C., the wells are rinsed with PBS, the adhering cells are then lyzed with 0.1 N sodium hydroxide solution and the cellular proteins are then quantified by means of the colorimetric method and bicinchoninic acid (BCA from Sigma).

A calibration is performed in parallel with BSA solubilized in 0.1 N sodium hydroxide solution, enabling the optical density (OD) values to be converted to micrograms ($\mu$g) of proteins per well.

5. Statistical Analysis

The adhesion A is expressed in micrograms of cellular proteins per culture well and the values shown in Table I correspond to a mean value obtained from 6 wells per product concentration, the products being the untreated cells, the cells treated with a magnesium chloride or aspartate concentration of 0.25 mM, the cells treated with a magnesium chloride concentration of 0.5 mM and the cells treated with a magnesium chloride concentration of 1 mM.

These adhesion values between treated and untreated cells were compared by the Student t-test at the p=0.05 threshold in order to assess their level of significance.

The results obtained from the experiment on the keratinocytes of a 53-year-old donor are listed in Table I below:

TABLE I

| | A | Standard deviation | Student t-test |
|---|---|---|---|
| Control | 3.52 | 0.9 | |
| Magnesium chloride (0.25 mM) | 4.32 | 0.7 | Not significant ($p = 0.12$) |
| Magnesium chloride (0.5 mM) | 4.54 | 1.1 | Not significant ($p = 0.1$) |
| Magnesium chloride (1 mM) | 4.57 | 0.75 | Significant ($p = 0.05$) |
| Magnesium aspartate (0.25 mM) | 5.39 | 0.8 | Significant ($p = 0.004$) |

A = adhesion in μg of protein per well (mean)

The results listed in Table I above show that, compared with the control cultures, there is an increase in the adhesion of the keratinocytes to the type IV collagen in the presence of magnesium chloride as from the 0.25 mM concentration, but this is only statistically significant as from 1 mM.

The percentage increase in adhesion obtained with magnesium chloride at the 1 mM concentration is +31.

As far as magnesium aspartate is concerned, this also promotes the adhesion of the keratinocytes, but more strongly than magnesium chloride. In fact, the increase in adhesion is highly significant as from the 0.25 mM concentration.

The percentage increase in adhesion obtained with magnesium aspartate at the 0.25 mM concentration is +54.

Under these conditions, it is thus seen that these magnesium salts, and more especially magnesium aspartate, are of particular value because they produce highly significant results at low doses, enabling them to be used at low concentrations and hence with a good degree of safety.

EXAMPLE 2 OF THE INVENTION

1. Composition of an anti-wrinkle cream

| | |
|---|---|
| Magnesium L-aspartate | 0.3 g |
| Dry extract of Potentilla erecta | 0.01 g |
| Hyaluronic acid (sodium salt) | 0.06 g |
| Glycerol | 5.15 g |
| Total dry extract of Centella asiatica | 0.1 g |
| Vitamin A palmitate solution (1 million IU/g) | 0.1 g |
| Vitamin E acetate | 0.5 g |
| Dry extract of Perilla | 0.5 g |
| O/W emulsion excipient plus perfume and preservatives | qsp 100 g |

2. Testing of this Cosmetic Composition for Evaluation of its Anti-wrinkle Efficacy A—Principle To evaluate the anti-wrinkle efficacy of this cosmetic product on "crow's feet", negative replicas of skin are made at time 0 and then after 28 days of twice daily application of the above composition in the form of a cream.

These replicas, illuminated by a glancing light casting shadows behind each wrinkle, are analyzed with the aid of a commercially available image-analyzing software, called "Quantirides", developed by MONADERM (Monaco).

B—Equipment

B.1—For taking Impressions

Adhesive rings from 3M, of internal diameter 24 mm and external diameter 40 mm, are used.

The product Silflo® from FLEXICO UK, based on a silicone polymer combined with a catalyst, is used to take impressions.

B.2—For analyzing the Impressions

The following are used:

a COHU 4910-RS 170 and CCIR Monochrome CCD camera, which is a high-definition and very low-noise camera equipped with a fixed-focus lens and an 18×108 mm F 2.5 manual zoom lens;

a real-time high-resolution image acquisition card;

a Monaspot glancing illumination lamp with an angle of incidence of 35°;

a Kaiser RS 1 tripod, a 450×500 mm anti-reflection matt black plate and a 1000 mm height-adjustable column graduated in centimeters, equipped with an RA1 projection arm;

a special support for positioning and orientating the replicas;

the above-mentioned Quantirides software; and a microcomputer and a printer.

C—Protocol

1. Volunteers 30 subjects aged between 34 and 59 years, comprising 29 women and 1 man, were selected.

2. Test Product

The test product is the composition in the form of a cream described above in section 1.

3. Application

The cosmetic composition is applied twice a day, in the morning and evening, to the whole of one temporal zone of the face (crow's foot) for 28 days. The amount applied can be estimated at about 1.5 to 2 mg per cm 2, depending on what the subject is accustomed to. The other, "untreated" temporal zone serves as the control.

For three days preceding the start of the test, and throughout the entire test, no other cosmetic product is used on the treated zone or the control zone.

4. Experimental Conditions

Temperature: from 20 to 22° C.

Relative Humidity: from 40 to 50%

An impression of the control and treated zones is made at time 0 and after 28 days of treatment. An adhesive ring is positioned over the study zone. A thin layer of Silflo®, mixed with a few drops of catalyst (3 drops per 3 g of Silflo®) immediately before use, is applied to the inside of the zone delimited by the ring. The paste must be spread carefully to avoid the formation of air bubbles. After polymerization of the paste, a drying time of 4 minutes 30 seconds, the ring is detached from the skin, bringing the replica with it. At the end of the study, these impressions are analyzed with the aid of the Quantirides software.

D. Parameters Studied

For each subject and for each side of the face, on D0 (the day before the first application) and D28 (day 28 of application) processing of the impressions by the image analyzer made it possible to calculate the following parameters representing the state of wrinkling of the skin:

a) the total surface area of the wrinkles in $mm^2$;

b) the number of wrinkles;

c) the total length of the wrinkles in mm;

d) the mean length in mm; and e) the mean depth in μm.

E. Processing of the Results: Change in the Treated Side and the Control Side
1. Calculation
Mean Variation of the Parameters The following is calculated for each site and each parameter:

$$\text{Variation} \cdot (\%) = \left(\frac{m(t) - m(0)}{m(0)}\right) \times 100$$

where m(t)=mean value of the parameter studied at time t
m(0)=mean value of the parameter studied at time 0

2. Statistical Significance

Wilcoxon Test

The non-parametric Wilcoxon test is used, which makes it possible to take account of the small number of subjects and is applicable to the in vivo study of biological parameters in humans.

A comparison of the paired series is made as follows: the difference is evaluated for each pair and the differences are then placed in increasing order of absolute value; it is also indicated for each one whether it is positive or negative, zero differences being eliminated.

The quantities to be considered are as follows:

M=sum of the ranks of negative difference
P=sum of the ranks of positive difference
T=the smaller of the two totals, M or P The significance limit accepted for n<10 persons is below 10%.

The significance limit accepted for n≧10 persons is below 5%.

The Wilcoxon test was applied to the difference (m(t)−m(0)) at the different times at the two sites in order to compare the change in the treated site with the change at the control site.

A Wilcoxon test was applied to the raw values at time 0 (m(0)) in order to compare the change in each site with time.

3. Results

The results obtained from the experiment are listed in Table II below.

The control and treated sites are comparable at time 0.

The values shown in column 4 under the heading "total variation" correspond to the difference between the variation in the treated subjects and the variation in the control subjects.

TABLE II

| | Variation in control subjects % | Variation in treated subjects % | Total variation % | Statistics (Wilcoxon) |
|---|---|---|---|---|
| Total surface area of wrinkles (mm²) | 6.6 | −19.7 | −26.3 | Significant (p = 0.015) |
| Number of wrinkles | 16.5 | −14.3 | −30.8 | Significant (p = 0.004) |
| Total length (mm) | 12.9 | −16.7 | −29.6 | Significant (p = 0.0014) |
| Mean length (mm) | −2.6 | −1.7 | 0.9 | Not significant |
| Mean depth (μm) | 0.3 | −2.0 | −2.3 | Not significant |

E. Conclusion

After twice daily application of the composition according to the invention for 28 days, the change in the treated crow's foot is compared with the change in the control crow's foot to reveal a significant decrease in the large and small wrinkles and a slowing-down of their formation: the total surface area of the wrinkles drops by 26%, their number by 31% and their total length by 30%.

EXAMPLE 3 OF THE INVENTION

W/O Anti-Wrinkle Night Cream

| | |
|---|---|
| Magnesium aspartate | 0.3 g |
| Dry extract of Potentilla erecta | 1 g |
| Glycerol | 5 g |
| Propylene glycol | 2 g |
| Ceramide III | 0.04 g |
| UV filters | 9 g |
| Methylsilanol mannuronate | 0.05 g |
| Dry extract of Perilla frutescens | 1 g |
| Dry extract of Centella asiatica | 0.5 g |
| Soya peptide | 1 g |
| Retinol palmitate | 0.2 g |
| W/O emulsion excipient | qsp 100 g |

EXAMPLE 4 OF THE INVENTION

Firming Cream for Slowing Down and Combating the Appearance of Wrinkles

| | |
|---|---|
| Magnesium aspartate | 0.2 g |
| Glycerol | 5 g |
| Propylene glycol | 2 g |
| Ceramide II | 0.04 g |
| Parsol MCX | 5 g |
| Oxybenzone | 3 g |
| Methylsilanol mannuronate | 0.05 g |
| Madecassoside | 0.5 g |
| Retinol | 4000 IU |
| Saponins from Medicago sativa | 0.02 g |
| Retinol palmitate | 0.04 g |
| O/W emulsion excipient | qsp 100 g |

EXAMPLE 5 OF THE INVENTION

Anti-wrinkle Tightening Gel

| | |
|---|---|
| Zinc gluconate | 0.3 g |
| Dry extract of Bertholletia excelsa | 0.3 g |
| Soya saponin | 0.05 g |
| Retinol palmitate | 0.06 g |
| Alpha-tocopherol acetate | 0.1 g |
| Lactic acid | 1.5 g |
| Glycolic acid | 0.2 g |
| Ethanol | 5 g |
| Gel excipient | qsp 100 g |

What is claimed is:

1. A method of cosmetic care for promoting the adhesion of the keratinocytes of the epidermal basal layer to the dermo-epidermal junction, comprising the steps of determination of the parts of the skin in need thereof and application to said parts of a cosmetic composition containing an active agent selected from the group consisting of magnesium salts, magnesium complexes, and mixtures thereof, in an efficient amount for promoting said adhesion.

2. The method according to claim 1, wherein said active agent is a magnesium salt.

3. The method according to claim 2, wherein said magnesium salt is magnesium chloride.

4. The method according to claim 1, wherein said active agent is a complex of magnesium with a cosmetically acceptable organic acid.

5. The method according to claim 4, wherein said complex is a complex of magnesium with an amino acid.

6. The method according to claim 5, wherein said complex of magnesium is a complex with an amino acid selected from the group consisting of aspartic acid, asparagine acid, proline, glutamic acid, methionine, leucine, histidine, and lysine.

7. The method according to claim 6, wherein said magnesium complex is magnesium aspartate.

8. The method according to claim 4, wherein said complex is a magnesium complex with a $C_2$–$C_{12}$ aliphatic alpha-hydroxy acid.

9. The method according to claim 8, wherein said $C_2$–$C_{12}$ aliphatic alpha-hydroxy acid is selected from the group consisting of citric acid, glycolic acid, gluconic acid, malic acid, lactic acid, and 2-hydroxybutyric acid.

10. The method according to claim 1, wherein said composition comprises between 0.0001 and 5% by weight of said active agent, based on the total weight of the composition.

11. The method according to claim wherein said composition comprises between 0.01 and 1% by weight of said active agent, based on the total weight of the composition.

12. The method according to claim 1, wherein said composition further comprises an effective amount of at least one agent stimulating the synthesis of collagen IV.

13. The method according to claim 12, wherein said agent stimulating the synthesis of collagen IV is selected from the group consisting of soya saponins, soya sapogenols, and mixtures thereof.

14. The method according to claim 12, wherein said agent stimulating the synthesis of collagen IV is an extract from roots of *Medicago sativa*.

15. The method according to claim 1, wherein said composition further comprises an active agent stimulating the synthesis of collagen VII.

16. The method according to claim 15, wherein said active agent stimulating the synthesis of collagen VII is an extract of *Potentilla erecta*.

17. The method according to claim 15, wherein said active agent for stimulating the synthesis of collagen VII is an extract of Bertholletia.

* * * * *